US012702653B2

(12) United States Patent
Cao

(10) Patent No.: US 12,702,653 B2
(45) Date of Patent: Aug. 11, 2026

(54) EYE DROPS WITH CITRIC ACID AS THE SOLE ACTIVE INGREDIENT

(71) Applicant: Jinan Cao, Forest Hill (AU)

(72) Inventor: Jinan Cao, Forest Hill (AU)

( * ) Notice: Subject to any disclaimer, the term of this patent is extended or adjusted under 35 U.S.C. 154(b) by 554 days.

(21) Appl. No.: 16/974,157

(22) PCT Filed: Apr. 28, 2019

(86) PCT No.: PCT/AU2019/050379
§ 371 (c)(1),
(2) Date: Oct. 26, 2020

(87) PCT Pub. No.: WO2019/210352
PCT Pub. Date: Nov. 7, 2019

(65) Prior Publication Data

US 2021/0228516 A1 Jul. 29, 2021

(30) Foreign Application Priority Data

May 1, 2018 (AU) ................................ 2018901462

(51) Int. Cl.
*A61K 31/194* (2006.01)
*A61K 9/00* (2006.01)
*A61K 9/08* (2006.01)

(52) U.S. Cl.
CPC .......... *A61K 31/194* (2013.01); *A61K 9/0048* (2013.01); *A61K 9/08* (2013.01)

(58) Field of Classification Search
CPC ....... A61K 9/0048; A61K 31/194; A61K 9/08
See application file for complete search history.

(56) References Cited

U.S. PATENT DOCUMENTS 1,808,737 A * 6/1931 Loesch ............... C08B 37/0048 536/2
8,648,057 B2 * 2/2014 Holzer ................. A61K 9/0048 536/55.1

FOREIGN PATENT DOCUMENTS

CN 101081205 A * 12/2007
JP 4065591 B2 * 3/2008

OTHER PUBLICATIONS

Invest Ophthalmol Vis. Sci. 1988 , 29(7):1110-5. Citrate or Ascorbate/Citrate Treatment of Established Corneal Ulcers in the Alkali-Injured Rabbit Eye (Year: 1988).*
JP 4065591 B2-Translation-Google Patents (Year: 2022).*
Cicinelli et al. (Lancet 2023; 401: 377-89, doi.org/10.1016/S0140-6736(22)01839-6), (Year: 2023).*
Weinreb et al. (JAMA. 2014;311(18):1901-1911. doi: 10.1001/jama.2014.3192), (Year: 2014).*
McKean-Cowdin et al. (Ophthalmology 2011; 118:1974-1981, doi:10.1016/j.ophtha.2011.06.031), (Year: 2011).*
Kojima, et al. (Progress in Retinal and Eye Research 78 (2020) 100842), doi.org/10.1016/j.preteyeres.2020.100842), (Year: 2020).*
CN 101081205A Translation (Year: 2007).*
JP 4065591B2 Translation (Year: 2008).*
FDA Glossary of Terms, Nov. 14, 2017, Retrieved from the internet Archive, website: https://www.fda.gov/drugs/drug-approvals-and-databases/drugsfda-glossary-terms. (Year: 2017).*
Scholtz S. History of Ophthalmic Viscosurgical Devices, 2007, CRST Global. Available from: crstodayeurope.com/articles/2007-jan/0107_06-php/. (Year: 2007).*

* cited by examiner

*Primary Examiner* — James H Alstrum-Acevedo
*Assistant Examiner* — Manahil Mirghani Ali Abdalhameed

(57) ABSTRACT

This patent application discloses a method of manufacturing eye drops that can be used to ameliorate or cure eye conditions such as cataracts, presbyopia, glaucoma, astigmatism, dry eye as well as for generic eye care uses. The sole active ingredient of said eye drops is citric acid—its aqueous solution around 0.9% by weight, which can be adjusted to either higher or lower levels of concentration according to clinical needs. Citric acid can be sourced either from industrial products or from natural fruits such as lemons and pineapples.

4 Claims, 1 Drawing Sheet

Chemical formula of citric acid: $C_6H_8O_7$

HO OH OH OH O O O

EYE DROPS WITH CITRIC ACID AS THE SOLE ACTIVE INGREDIENT

TECHNICAL FIELD

This invention provides details for manufacturing eye drops that ameliorate and cure eye conditions including cataracts, presbyopia, glaucoma, astigmatism and dry eye.

BACKGROUND ART

There are several eye conditions that lead to decrease in vision primarily due to aging. When one grows old, the lens of the eye may get cloudy that leads to senile cataracts; and the lens gets stiffer and stiffer that leads to presbyopia. When the eye's trabecular meshwork becomes clogged or blocked, the intraocular pressure will be elevated, leading to an eye condition called glaucoma.

Clouding of the lens causes cataracts. It develops slowly and progressively with aging, resulting in reduced visual acuity and problems such as faded colours and blurry vision etc. Severe cataract eventually leads to blindness if left untreated.

The most effective treatment of cataracts is surgery, which removes the clouding natural lens of the eye, then inserts an artificial intraocular lens to restore the lens's transparency. Successful rate of surgical operations is high. However, cataract surgery is generally performed by an ophthalmologist in an ambulatory setting, in a surgical centre or hospital under anaesthesia. For a small group of people, e.g. severe diabetes patients or patients who do not have reasonable health conditions, the risk is too high to have a surgery. Therefore, cataract treatment using eye drops is desirable and appealing.

There are a number of commercially available eye drop products on the market claiming curing cataracts. N-Acetylcarnosine eye drops have being investigated as a medical treatment alternative to surgery for cataracts (Mark Thierman, U.S. Pat. No. 7,776,364B2, 2010). The drops are believed to work by reducing oxidation and glycation damage in the lens, particularly reducing crystalline cross-linking. Some benefit has been shown in small manufacturer sponsored randomized controlled trials but further independent corroborations are still required to confirm the benefit. Eye drop products similar to N-Acetylcarnosine, such as Can-C, Herbal Isotine Eye Drop Cataract, are also commercially available on the markets.

In the domain of patents, disclosures of invention of eye drops for curing cataracts are one after another. J. Stjernschantz; Resul; B. Resul disclosed an invention entitled "Method and means for prevention of cataract" (U.S. Pat. No. 5,773,472, 1998). It claims an invention of thiol-binding prostaglandins or prostaglandin-like substances containing alpha beta unsaturated ketone, esp. prostaglandins of type A or J and derivatives or analogues thereof, for the preparation of ophthalmically compatible compositions for prevention of cataracts.

M. Terao and Y. Ito claimed a "Method for Treatment of Cataract with Radical Scavenger" (U.S. Pat. No. 5,874,455, 1999). The patent application states: the invention provides a method for treatment of cataract which comprises administering to a subject in need of such treatment, a radical scavenger in an amount effective in treatment of cataract selected from the group consisting of a reducing thiol derivative, or a disulfide derivative and a sulfide derivative thereof, and a pharmaceutical composition for treatment of cataract which comprises an anti-cataract agent containing a radical scavenger and fine particles, such as emulsions, nanocapsules, albumin microspheres and liposomes, which carries an anti-cataract agent and has a lipophilic and positively charged phase on the surface thereof.

Another US patent, US 2014/0031327A1, discloses an invention using inhibitors of a-crystalline aggregation to treat or prevent cataracts in a subject having or at risk of developing cataracts.

Several patent applications for treatment of senile cataracts by traditional Chinese medicine eye drops have been filed. For example, Du Xiulan et al. disclosed in 2009 a traditional Chinese Medicine for Treating Senile Cataract (WIPO Application Number: 200910018921). X. Zhao disclosed "Eye Drop for Treating Cataract" (Europe Patent Office: CN104208315 (A), 2014). The eye drop is prepared from inula flower, kelp, *fructus lycii, chrysanthemum, schisandra chinensis*, glossy privet fruit, *rhizoma acori graminei, semen plantaginis* and *angelica sinensis*, with its aim at providing a medicine for treating cataract with an exact curative effect. Furthermore, D. Song et al. disclosed in 2014 a "Traditional Chinese medicine for treating cataract" (WIPO: Application Number: 201410191869.9). The recipe comprises *ginseng*, unprepared *rehmannia* root, *fructus leonuri*, abalone shell, *radix platycodonis, semen plantaginis*, white peony root, Manchurian wildginger, *Rheum officinale, Semen cassiae, Eriocaulon buergerianum, Radix Paeoniae Rubra, Ligustri Lucidi fructus, flos buddlejae*, white *chrysanthemum*, Flatstem Milkvetch seed, *Tribulus terrestris, Radix codonopsis, Radix astragali, Radix scutellariae* and honey-fried licorice root.

While the lens becomes cloudy losing transparency for senile cataracts, the lens becomes stiffer progressively diminishing ability to focus on near objects for presbyopia. Medical evidence so far strongly supports the interpretation of hardening of the eye lens, although some believe that changes in the lens curvature and loss of power of the ciliary muscles could also be the causes.

Reading glasses are the simplest and most common treatment for presbyopia. A reading glass provides an extra dioptre to enhance eye accommodation so that near objects can be seen clearly. Contact lenses are an approach similar to reading glasses.

Another treatment for presbyopia is surgery to reshape the cornea, so that the eye has more accommodation power. The surgical technology is successful, but it is reported that some use of reading glasses will still remain when light is dim, or when reading for prolonged periods of time. There are also alternative surgical procedures for correction of presbyopia without reshaping the cornea. For example, Scharcker and Lin proposed a treatment using a laser ablation technology for scleral band expansion in an U.S. Pat. No. 6,258,082 (2001). There are various other surgical technologies for treatment of presbyopia as well.

Apart from surgery, treatments using medicine drugs are an area of research. J. Benozzi, G. Benozzi and B. Orman proposed a new pharmacological treatment for presbyopia (Med. Hypothesis Discov. Innov. Ophthalmol. 2012 Spring; vol 1(1), pages 3-5). It was suggested that the correction of accommodation in emmetropic presbyopic patients can be achieved by a pharmacological treatment that includes a cholinergic agent combined with non-steroidal anti-inflammatory drugs. This drug combination is claimed potentially able to restore near vision without affecting distance vision.

There are also claims that proteins, vitamins and/or exercises help treat presbyopia. Ethos Bright Eyes is a commercially available eye drop product, claiming that N-acetyl-Carnosine or NAC, a very powerful antioxidant and antiglycating agent, treats presbyopia by leading to a slower and even reversed biological aging process.

Presbyopia is truly a subject of patent applications. Muthukumar et al. disclosed "Methods of Inhibiting Cataracts and Presbyopia" in 2014 (U.S. Pat. No. 8,758,802). The inventors consider that presbyopia and cataracts are caused by aggregation of a soluble beta.sub.L-crystallin protein in the lens; therefore, electrostatic interaction inhibitors can be employed to inhibit or reverse the progression of cataract formation or presbyopia. Kaufman disclosed a patent "Preparations and Method for Ameliorating or Reducing Presbyopia" in 2013 (U.S. Pat. No. 8,455,494), which relates to the use of one or more parasympathomimetic drugs in combination with one or more alpha agonists to create optically beneficial miosis to temporarily treat presbyopia. In addition, Garner et al. disclosed a patent entitled "Dithiol Compounds, Derivatives, and Treatment of Presbyopia" in 2014 (U.S. Pat. No. 8,647,612). Dithiol agents are claimed useful for treating ocular disease, especially presbyopia and cataracts.

Glaucoma is usually, but not always, associated with elevated intraocular pressure in the eye. When the eye's trabecular meshwork becomes clogged or blocked, the intraocular pressure will be elevated, leading to damage of the eye optic nerve.

There are several surgical treatments available to remove the clogged trabecular meshwork and to create a new drainage pathway for the fluid to exit the eye. Laser iridotomy involves making a hole in the iris to allow fluid to drain normally for treatment of the angle closure glaucoma. And various laser technologies are available to burns the clogged meshwork to allow better drainage of the aqueous humour for open angle glaucoma.

Various eye drop products, such as timolol (Timoptic), levobunolol (Betagan), carteolol (Ocupress), and metipranolol (Optipranolol) are available for treatment of glaucoma by reducing production of the aqueous humour. Another type of eye drops such as prostaglandin analogs work in glaucoma by increasing the outflow (drainage) of fluid from the eye to restore normal intraocular pressure. These eye drops do not cure glaucoma, and often have systemic side effects, including reduction of body potassium, kidney stones, numbness or tingling sensations in the lips, arms, and legs, fatigue, and nausea.

The preceding discussion of the background to the invention is intended to facilitate an understanding of the present invention. It is not an acknowledgement or admission that any of the material referred to was part of the common general knowledge as at the priority date of this present application.

SUMMARY OF INVENTION

This invention discloses that citric acid is a useful pharmaceutical composition for eye drops that can be used to clean the cornea and the lens to cure or ameliorate cataracts, astigmatism and dry eye, to soften the lens to cure or ameliorate presbyopia, and to dredge the trabecular meshwork to cure or ameliorate glaucoma. Citric acid can be sourced either from industrial products or from natural fruits such as lemons and pineapples. Use of said eye drops results in improvement in visual acuity.

BRIEF DESCRIPTION OF DRAWINGS

A preferred embodiment of the present invention will now be described, by way of an example only, with reference to the accompanying drawings wherein:

FIG. 1 shows the chemical formula and structure of citric acid.

DESCRIPTION OF EMBODIMENTS

Useful eye drops must be able to dissolve aggregated proteins in the lens of the eye so that the lens becomes less cloudy and more transparent, to soften the lens so that it can be more focused on near objects. Eye drops that can dissolve the proteins that clog the trabecular meshwork will allow aqueous humour to flow normally. Citric acid is found to possess these desired properties dissolving aggregated and clogged proteins in the cornea, the lens and the trabecular meshwork; it can be used to make eye drops that cure or ameliorate cataracts, presbyopia, glaucoma, astigmatism and dry eye, as well as improve visual acuity for generic eye cares.

Citric acid has a chemical formula of $C_6H_8O_7$. FIG. 1 shows its full chemical structural details. It is a weak organic acid with strong natural preservative power. As an antimicrobial additive and antioxidant, it is often used in products such as foods, pharmaceuticals and biological samples to prevent decomposition by microbial growth.

Citric acid has a molar mass 192.12 g/mol and a density greater than 1.5 g/cm$^3$. Small molecules are ideal for corneal permeation to enter into the anterior chamber so that the eye drops can effectively reach the lens and the trabecular meshwork. Taking advantage of the high density heavier than water, a user would be better facing up while instilling so that citric acid molecules that have permeated the cornea have more chances to act with the lens. Note that the volume of the anterior chamber of the eye is around 250 μL, the concentration of citric acid in the eye drops is significantly diluted after corneal permeation.

Citric acid has a high melting point of 156° C. and a boiling point of 310° C. It would be a problem if it crystallises in the eye into nano or micro solid particles that will scatter light as a cataract lens does. However, its solubility in water reaches 147.76 g/100 mL at 20° C., 180.89 g/100 mL at 30° C. and 220.19 g/100 mL at 40° C., indicating that it is unlikely to crystallise into nano- or micro- solid particles in the eye as a result of use of said eye drops.

Ocular and intraocular compatibilities are a must for eye drops. This limits the highest concentration of citric acid in said eye drops. In general, the higher concentration would have higher efficiency. Lower concentration would have slower effect but less sting. Practically citric acid concentration in said eye drops can be about 1.0%; which can be varied either to a higher level to or to a lower level between about 0.2% by weight and about 1.8% by weight according to clinical needs.

Citric acid's aqueous solutions constitute of said eye drops of this present invention. Citric acid can be either sourced from products of industrial production or from extraction of natural products. Dissolving controlled amount of citric acid crystal into distilled water forms said eye drops, followed by necessary sterilisation processes. On the other hand, a number of citrus fruits such as lemon, orange and pineapples contain citric acid.

A ripe pineapple was cut off its skin, and the core was removed off. It was then chopped into small pieces, which were squeezed to obtain yellowish juice using a squeezer. The juice was then filtered using filter papers. Said eye drops were made by extracting citric acid from the juice and by adjusting its concentration to around 1.0% by weight. Preparation of said eye drops completed following necessary sterilisation processes.

Prior to application of said eye drops, shake it to mix well. This is because citric acid has a much higher density of 1.665 g/cm$^3$ than that of water 1.0 g/cm$^3$. One or two drops of said eye drops can be instilled each time for each eye. A user keeps facing up after instillation of said eye drops for 1-2 minutes or longer so that more citric acid can reach and permeate into the lens. 3-5 times each day, and 5-7 days of said eye drops can be applied as a course of treatment. Users may tell improvement in terms of visual acuity during or after the first course of treatment. Further courses of treatment can be performed if want after 2-4 weeks or longer.

Citric acid level in said eye drops can be diluted or concentrated. To dilute said eye drops, add controlled amount of distilled water in and shake to mix it. To concentrate, evaporate controlled amount of water in the eye drops by boiling it.

It will be mildly sting for the first several seconds when said eye drops are instilled to the eye. For users who feel too sting, said eye drops can be diluted to a lower level, e.g. 50%, or 25% or 12.5%. After practice of the low concentration said eye drops, the users get used to and feel less sting. The users can then instil said eye drops with higher concentration of citric acid.

Users may get the eye slightly irritated as a result of stimulation of said eye drops. Stop use of said eye drops and wash the eye using clean tap water or distilled water. Application of said eye drops can resume when the users feel comfortable.

Inactive ingredients may be added to said eye drops as preservatives or as lubricants for any desired functionalities if necessary.

It is not recommended to apply said eye drops while one suffers eye diseases such as conjunctivitis, pink eye and sty; or shortly after any eye operation.

CITATION LIST

Patent Literature

U.S. Pat. No. 7,776,364B2, 2010 [0005]

U.S. Pat. No. 5,773,472, (1998) [0006]

U.S. Pat. No. 5,874,455, (1999) [0007]

United States Patent, US 2014/0031327A1 (2014) [0008]

WIPO Application Number: 200910018921 [0009]

Europe Patent Office: CN104208315 (A), (2014) [0009]

WIPO: Application Number: 201410191869.9, (2014) [0009]

U.S. Pat. No. 6,258,082 (2001) [0012]

U.S. Pat. No. 8,758,802, (2014) [0015]

U.S. Pat. No. 8,455,494, (2013) [0015]

U.S. Pat. No. 8,647,612, (2014) [0015]

Non-Patent Literature

Ethos Bright Eyes, N-acetyl-Carnosine or NAC: https://www.ethoseyesite.com/index.html, accessed on Jul. 17, 2018 [0005], [0014]

J. Benozzi, G. Benozzi and B. Orman; Med. Hypothesis Discov. Innov. Ophthalmol. 2012 Spring; vol 1(1), pages 3-5, [0013]

The invention claimed is:

1. A method of curing cataracts, presbyopia, glaucoma and astigmatism, comprising administering eye drops, wherein said eye drops consist of citric acid as the sole active ingredient, water, and optionally one or more ophthalmically acceptable inactive ingredients selected from preservatives and lubricants, wherein said inactive ingredients do not neutralize or chelate citric acid.

2. The method according to claim 1 wherein citric acid is in aqueous solution and, wherein citric acid is present in concentration range of 0.2 wt % to 1.8 wt %.

3. The method according to claim 1 or claim 2 wherein citric acid is sourced from industrial products.

4. The method according to claim 1 or claim 2 wherein citric acid is extracted from lemons and pineapples by filtering, precipitation, evaporation, crystallisation and diluting.

* * * * *